(12) United States Patent
Westrum, Jr.

(10) Patent No.: US 7,066,876 B2
(45) Date of Patent: Jun. 27, 2006

(54) METHOD FOR DETECTING AN UNSATISFACTORY CONDITION IN AN IMPLANTABLE SYSTEM

(75) Inventor: John W. Westrum, Jr., Prior Lake, MN (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

(21) Appl. No.: 11/157,653

(22) Filed: Jun. 21, 2005

(65) Prior Publication Data

US 2005/0228220 A1    Oct. 13, 2005

Related U.S. Application Data

(62) Division of application No. 10/431,715, filed on May 8, 2003, now Pat. No. 6,929,599.

(60) Provisional application No. 60/380,684, filed on May 14, 2002.

(51) Int. Cl.
    *A61F 5/00* (2006.01)
(52) U.S. Cl. .................................................. 600/38
(58) Field of Classification Search ............ 600/38–41, 600/29–31; 128/897–898
    See application file for complete search history.

(56) References Cited

U.S. PATENT DOCUMENTS

| | | |
|---|---|---|
| 3,853,122 A | 12/1974 | Strauch et al. |
| 3,954,102 A | 5/1976 | Buuck |
| 3,987,789 A | 10/1976 | Timm et al. |
| 4,009,711 A | 3/1977 | Uson |
| 4,244,370 A | 1/1981 | Furlow et al. |
| 4,350,151 A | 9/1982 | Scott |
| 4,537,183 A | 8/1985 | Fogarty |
| 4,559,931 A | 12/1985 | Fischell |
| 4,566,446 A | 1/1986 | Fogarty |
| 4,628,912 A | 12/1986 | Fischell |
| 4,651,721 A | 3/1987 | Mikulich et al. |
| 4,653,485 A | 3/1987 | Fischell |
| 4,766,889 A | 8/1988 | Trick et al. |
| 4,881,530 A | 11/1989 | Trick |
| 5,048,511 A | 9/1991 | Rosenbluth et al. |
| 5,141,509 A | 8/1992 | Burton et al. |
| 5,167,611 A | 12/1992 | Cowan |
| 5,250,020 A | 10/1993 | Bley |
| 5,518,499 A | 5/1996 | Agar |
| 5,788,627 A | 8/1998 | Subrini |
| 5,851,176 A | 12/1998 | Willard |

(Continued)

OTHER PUBLICATIONS

Mentor Urology Products, Mentor Corp., (May 1998).

(Continued)

*Primary Examiner*—Samuel G. Gilbert
(74) *Attorney, Agent, or Firm*—Kimberly K. Baxter (57) ABSTRACT

Surgical implants and procedures for restoring erectile function are described. A method of detecting an unsatisfactory condition of an inflatable penile prosthesis system including a pump, cylinder(s), fluid circuit, a septum and a reservoir. The method including the steps of: i) implanting the inflatable penile prosthesis system in a patient; ii) providing a probe assembly with first and second sensors; iii) placing the first sensor through the septum and into the fluid circuit of the inflatable penile prosthesis system; iv) placing a second sensor outside the penile prosthesis system in the patient's tissue, v) sensing conditions with the first and second sensors, and vi) comparing the conditions sensed by the first and second sensors to detect an unsatisfactory condition.

7 Claims, 9 Drawing Sheets

U.S. PATENT DOCUMENTS

| | | |
|---|---|---|
| 6,443,887 B1 | 9/2002 | Derus et al. |
| 6,533,719 B1 | 3/2003 | Kuyava et al. |
| 6,534,112 B1 | 3/2003 | Bouchier et al. |
| 2003/0233126 A1* | 12/2003 | Kaplan et al. .................. 607/3 |

OTHER PUBLICATIONS

700 Ultrex™ Plus Penile Prostheses, American Medical Systems, 2 pages (1999).

AMS 700 CX™ Penile Prosthesis, American Medical Systems, 2 pages (1999).

Mark II Inflatable Penile Prosthesis, Mentor Corp., (1990).

Surgical Protocol, Alpha I® Inflatable Penile Prosthesis, Mentor Corp., (Feb. 1998).

Mentor, Alpha I® Inflatable Penile Prosthesis, 17 pages, (Jul. 2000).

* cited by examiner

METHOD FOR DETECTING AN
UNSATISFACTORY CONDITION IN AN
IMPLANTABLE SYSTEM

CROSS REFERENCE TO RELATED APPLICATION

This is a divisional of U.S. patent application Ser. No. 10/431,715, filed on May 8, 2003, now U.S. Pat. No. 6,929,599, which Application claims the benefit of U.S. Provisional Patent Application No. 60/380,684 filed May 12, 2002, both of which are fully incorporated herein by reference.

BACKGROUND

The present invention relates to medical devices used in implant surgery. More specifically, the present disclosure relates to an inflatable penile prosthesis assembly, or penile implant.

Even as late as the early 1970's, the conventional view of impotence was that ninety percent of cases were psychologically based, whereas only ten percent of the cases were caused by a physical condition. Today, doctors and scientists understand that the overwhelming majority of cases are caused by a physical condition. According to a recent study, fifty-two percent of men between the ages of forty and seventy self-reported that they suffer from some type of erectile dysfunction. Another study estimated that over thirty million American men and their partners suffer from erectile dysfunction.

Advertisements for pharmaceutical treatments for impotence have become ubiquitous. More and more men and their partners now are seeking treatment for impotence. In the recent past, it was estimated that only one in twenty sufferers of erectile dysfunction sought treatment from their doctors. Pharmaceutical treatments are successful for only a subset of impotence sufferers. Other treatments, including more invasive treatments are necessary for many men. These treatments include injection therapy, vacuum devices and penile prosthesis.

Penile implants are disclosed in U.S. Pat. Nos. 3,853,122; 4,009,711; 3,954,102; 4,537,183; 4,566,466; 3,987,789; 4,350,151; 5,788,627 4,651,721 5,141,509; 5,851,176; 5,167,611; 6,443,887 and 6,533,719. Commercial examples of penile prosthesis include the AMS 700 CX™ and the AMS 700 Ultrex™ available from American Medical Systems of Minnetonka, Minn. and the Mark II Inflatable Penile Prosthesis previously available from Mentor of Santa Barbara, Calif. The Mark II prosthesis included an injection port in a resipump element.

The penile implant has been used for decades and provides a selected and reliable erection. Inflatable penile implants typically include a pair of cylinders. In some instances, these cylinders are connected to a fluid-filled reservoir with a pump and valve assembly. The two cylinders are normally implanted into the corpus cavernosae of the patient's penis and the reservoir is typically implanted into the patient's abdomen. The pump assembly is implanted in the scrotum. During use, the patient actuates the pump and fluid is transferred from the reservoir through the pump and into the cylinders. This results in the inflation of the cylinders and produces rigidity for a normal erection. Then, when the patient desires to deflate the cylinders, a valve assembly within the pump is actuated in a manner such that the fluid in the cylinders is released back into the reservoir. This deflation returns the penis to a flaccid state.

A type of inflatable penile implant includes one or more cylinder(s) having inflation chamber(s) that are disposed within the penis (corpus cavernosae). The penile implant includes a remote pump assembly that is connected via tubing to the cylinder(s). The tubing is connected to the cylinder(s) at tubing junction(s). In prior art examples, such as those in United States Patent Nos. among others, show a straight bore extending through the strain relief and into the inflation chamber. Fluid is transferred from the pump assembly, through the tubing, and into the cylinder(s).

Prior art methods for implanting inflatable prostheses typically included the step of leaving the cylinders inflated or partially inflated in the immediate post operative period. This allows the tissue surrounding the cylinder to heal while the cylinder is in an inflated condition. However, in systems that include a balloon like reservoir, this meant that the balloon-like reservoir was in a deflated or partially empty condition. In the prior art procedures, the body healed with the reservoir in such a condition. Unfortunately, scar tissue can form that can result in discomfort or pain when the reservoir was thereafter filled. It is also believed that the scar tissue can cause the cylinder(s) of the system to partially inflate at unintended times or prevent the cylinder(s) of the system from completely deflating.

U.S. Pat. No. 5,250,020 discloses a unitary inflatable penile prosthesis. This prosthesis includes an injection port with flexible silicone rubber. The injection port is said to be capable of partially prefilling the prosthesis at the time of manufacture, thereby relieving the surgeon of the task of assembling the components at the time of implantation.

U.S. Pat. No. 4,766,889 discloses an infusion erectile system. The system includes a septum and reservoir.

Some patients or surgeons complain of penile shaft shortening and/or insufficient cylinder flaccidity following penile implantation surgery. Although rare, some penile implants become infected and leaks in the hydraulic system develop in some.

SUMMARY OF THE INVENTION

In one aspect, the present invention comprises a septum in an inflatable penile prosthesis system that affords post-operative period access to the interior of the system. This allows both the reservoir and cylinders to be in a filled condition in the immediate post operative period.

According to one embodiment, the present invention comprises a method of restoring erectile function comprising the steps of: i) providing an inflatable penile prosthesis system comprising a pump, at least one and preferably two cylinders capable of inflated and deflated states, a septum and a reservoir capable of inflated and deflated states; ii) providing sufficient fluid to inflate the cylinder(s) and the reservoir to the inflated condition; iii) implanting the inflatable penile prosthesis system with the cylinder(s) and reservoir in the inflated condition; iv) leaving the cylinder(s) and reservoir in the inflated condition in the immediate post operative period, and v) thereafter inserting a needle through the septum and withdrawing some fluid from the inflatable penile prosthesis system. Preferably, the step of leaving the cylinder(s) and reservoir in the inflated condition in the immediate post operative period includes the step of leaving the cylinder(s) and reservoir in the inflated condition for at least three days, more preferably at least seven days.

In another aspect, the invention comprises a method of detecting an unsatisfactory condition of an inflatable penile prosthesis system comprising a pump, cylinder(s), fluid circuit, a septum and a reservoir. The method comprises the steps of: i) implanting the inflatable penile prosthesis system in a patient; ii) providing a probe assembly with first and second sensors; iii) placing the first sensor through the septum and into the fluid circuit of the inflatable penile prosthesis system; iv) placing a second sensor outside the penile prosthesis system in the patient's tissue, v) sensing conditions with the first and second sensors, and vi) comparing the conditions sensed by the first and second sensors to detect an unsatisfactory condition. The unsatisfactory condition may comprise fluid leakage or infection. The first and second sensors may be capable of sensing pH, electrical resistance or electrical potential. In the later case, the probe system may comprise an ohmmeter. In a preferred embodiment, at least one of the first and second sensors is integrated into the inflatable penile prosthesis system, and the probe system includes means for communicating with the sensor integrated into the inflatable penile prosthesis system.

In another aspect, the present invention comprises a system for restoring erectile function comprising a pump, cylinder(s), tubing and a reservoir, a fluid circuit within the system containing fluid, a septum, and an antimicrobial or antibiotic within the fluid placed by inserting a needle through the septum and injecting the antimicrobial or antibiotic. For example, the antimicrobial or antibiotic may comprise rifampin and minocycline. Alternatively, an antimicrobial may comprise an iodine containing compound.

In yet another aspect, the present invention comprises a method of restoring erectile function comprising the steps of: implanting an inflatable penile prosthesis having fluid and a septum, placing a needle through the septum, and injecting an antimicrobial through the septum and into the prosthesis. In a preferred embodiment, the prosthesis comprises cylinder(s) comprising silicone, and the antimicrobial comprises iodine. Preferably, the method further includes the step of aspirating fluid from the inflatable penile prosthesis prior to the step of injecting an antimicrobial. Alternatively the antibiotic solution may be infused.

BRIEF DESCRIPTION OF THE DRAWINGS

Other features and advantages of the present invention will be seen as the following description of particular embodiments progresses in conjunction with the drawings, in which.

DETAILED DESCRIPTION

The following description is meant to be illustrative only and not limiting. Other embodiments of this invention will be apparent to those of ordinary skill in the art in view of this description.

Figure 1:
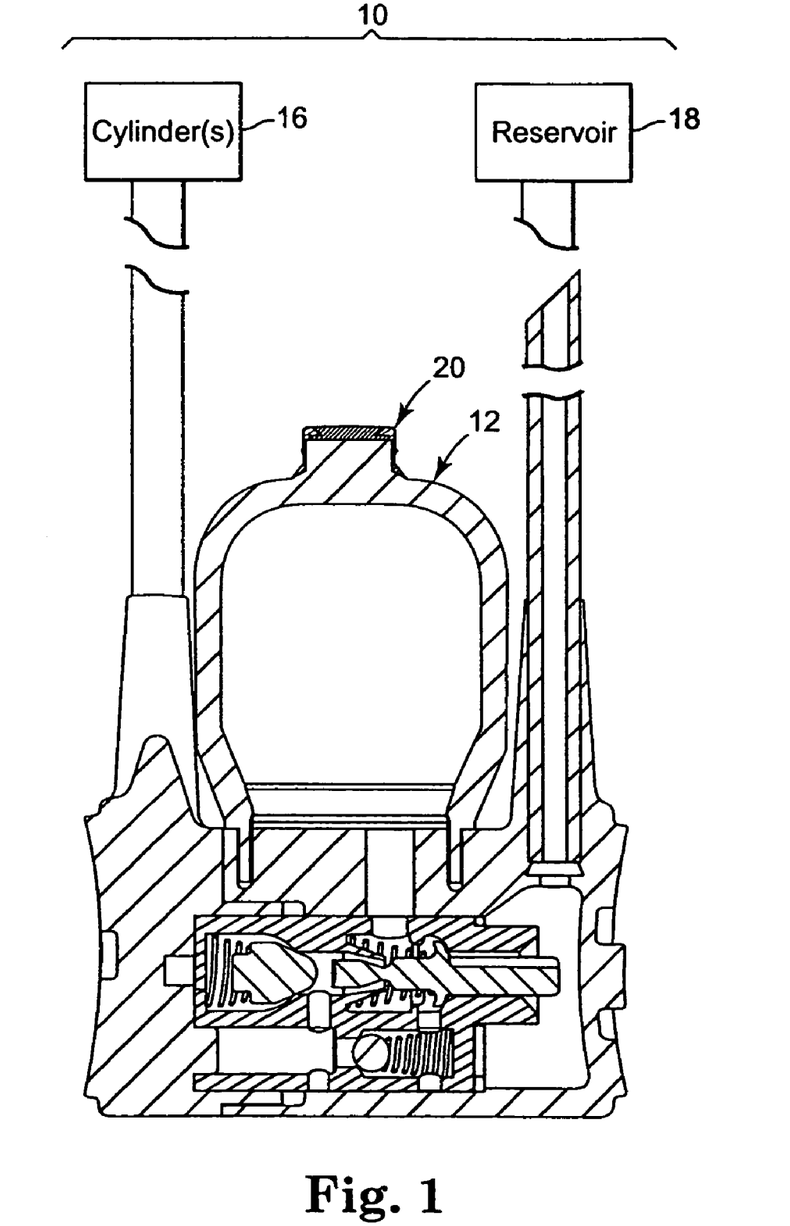
FIG. 1 is a schematic view of a three piece embodiment of the present invention showing a pump bulb and a fluid septum.
Figure 2:
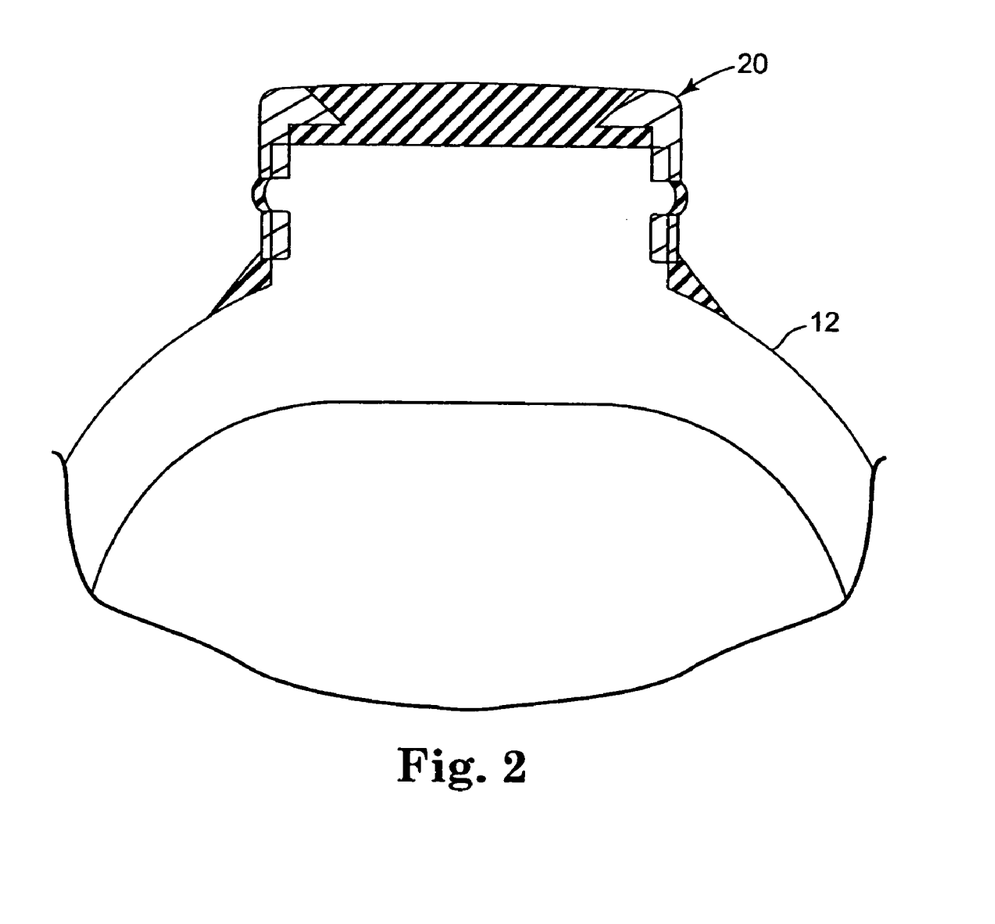
FIG. 2 is an enlarged sectional view of a portion of the pump bulb and septum of FIG. 1.
Figure 3:
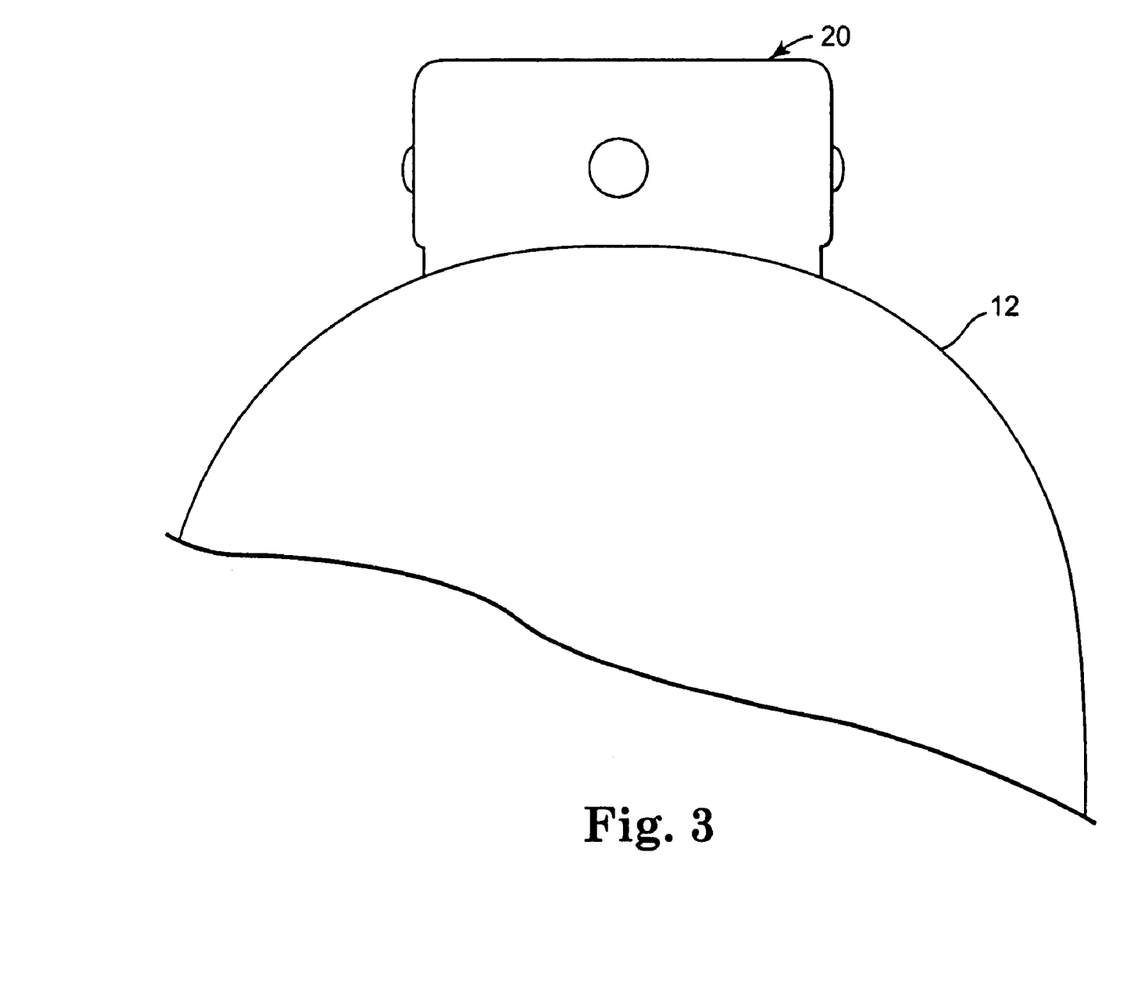
FIG. 3 is a side view of the components of FIG. 2.

Referring now to FIGS. 1, 2 and 3, there is shown components of an inflatable penile prosthesis system suitable for use in a method according to the present invention. The system 10 comprises a pump (e.g. a pump bulb 12), at least on and preferably two cylinders 16 capable of inflated and deflated states, septum 20 and reservoir 18 capable of inflated and deflated states. Suitable cylinders, pumps and reservoirs are disclosed in U.S. Provisional Patent Application No. 60/453,684 and published U.S. Pat. Application Nos. 2003/0065249-A1; 2003/0028076-A1; 2002/0091302-A1; 2002/0082709-A1; 2002/0082708-A1; 2002/0082473-A1; and 2002/0082471-A1; and U.S. Pat. Nos. 6,346,492; 6,443,887 and 6,558,315.

As used herein, a septum 20 is an article constructed from a biocompatible (preferably non-porous) material that can be pierced repeatedly without leaking fluids or bacteria. Soft silicone rubbers are believed suitable for such products. Suitable materials include silicones, rubbers, polymers and combinations thereof. Commercial examples include Nusil 4750 silicone, Nusil 4735 and Nusil 4720 silicones available from Nusil of Carpenteria, Calif. In a preferred embodiment, the septum 20 is replaceable so that it could be replaced (e.g. during a revision surgery). Alternatively, the septum 20 may comprise a permanent septum.

Preferably the septum is sized and shaped to afford access to the interior of the prosthesis without unduly irritating tissue. For example, the septum may be between 4 and 8 mm in diameter with a height of between about 3 and 5 mm. Alternatively, the septum may be sufficiently large to act as a pump for pumping fluid or creating pressure surges. In an alternative embodiment, the septum may be used to activate a system. The device could remain inflated for a specific period of time and then become deactivated through the same septum or would gradually deflate by accelerated osmosis or a calibrated leak path that affords slow leakage over time. Fluid could be absorbed by the body or vascular system. Optionally, activation could be through a transcutaneous port that that includes a septum and which leads to the device via tubing.

In another embodiment, the septum may be placed on the interior of the pump bulb 12 or include shielding to reduce the chance of inadvertent damage to the prosthesis or positioning probes.

The system may be used in a method of restoring erectile function. The method generally includes the steps of i) implanting a system that is overfilled with fluid to inflate both the reservoir and the cylinder(s), ii) waiting until the body has sufficiently healed, and iii) then removing excess fluid. The method comprises the steps of: providing the inflatable penile prosthesis system 10; providing sufficient fluid to inflate the cylinder(s) 16 and the reservoir 18 to the inflated condition; implanting the inflatable penile prosthesis system 10 with the cylinder(s) and reservoir in the inflated condition; leaving the cylinder(s) 16 and reservoir 18 in the inflated condition in the immediate post operative period, and thereafter inserting a needle through the septum 20 and withdrawing some fluid from the inflatable penile prosthesis system. Preferably only the excess fluid is removed after healing, leaving the optimum amount of fluid in the system. Also preferably, the step of leaving the cylinder(s) and reservoir in the inflated condition in the immediate post operative period includes the step of leaving the cylinder(s) and reservoir in the inflated condition for at least three days, more preferably at least seven days.

The septum 20 allows the surgeon to leave both reservoir 18 and the cylinder(s) 16 fully inflated in the immediate post operative period, allowing the body to heal in the best possible configuration with a fully extended capsule around the cylinder(s) 16 and a full size capsule around the reservoir 18. Preferably, the reservoir 18 and cylinder(s) 16 remain in the fully inflated condition at least two days following the surgical procedure and more preferably at least three. The amount of time period may vary due to a variety of factors such as the condition of the particular patient, the presence of concomitant procedures and the ability to schedule a follow up visit and the like. In some cases, seven days may be desirable.

Preferably, the surgeon implants the system with the cylinder(s) 16 left nearly fully inflated in the post operative period. It is believed that such a step would reduce the chances of hematoma and allow the capsule around the cylinder(s) and reservoir to form at a fully distended condition. It is also believed to maintain penile shaft length following surgery. Following a time period, the surgeon uses the septum 20 to remove fluid from the system to the point of satisfactory flaccidity.

Should the reservoir 18 ever become encapsulated with significant scar tissue, the septum 20 allows the surgeon to fill the cylinder(s) 16 and the reservoir 18 and allow the power provided by the cylinder(s) 16 to gradually distend the capsule of the reservoir 18. The surgeon could exploit the additional fluid in the cylinder(s) 16 to force fluid back into the reservoir 18, again leaving the cylinders 16 fully inflated to allow capsule formation at the greatest diameter of the reservoir 18.

With the septum 20, fluid may be added or removed from the hydraulic system without disconnecting and reconnecting components (e.g. tubing). The septum 20 could also be used if needed to add fluid to a system where additional fluid requirements emerged over time. For example, this may occur where the shaft length and cylinder volume requirements change with time and the initial reservoir was insufficient to accommodate the change. Such occurrence can occur in patients with significant scarring from disease processes or previous surgery.

Figure 4:
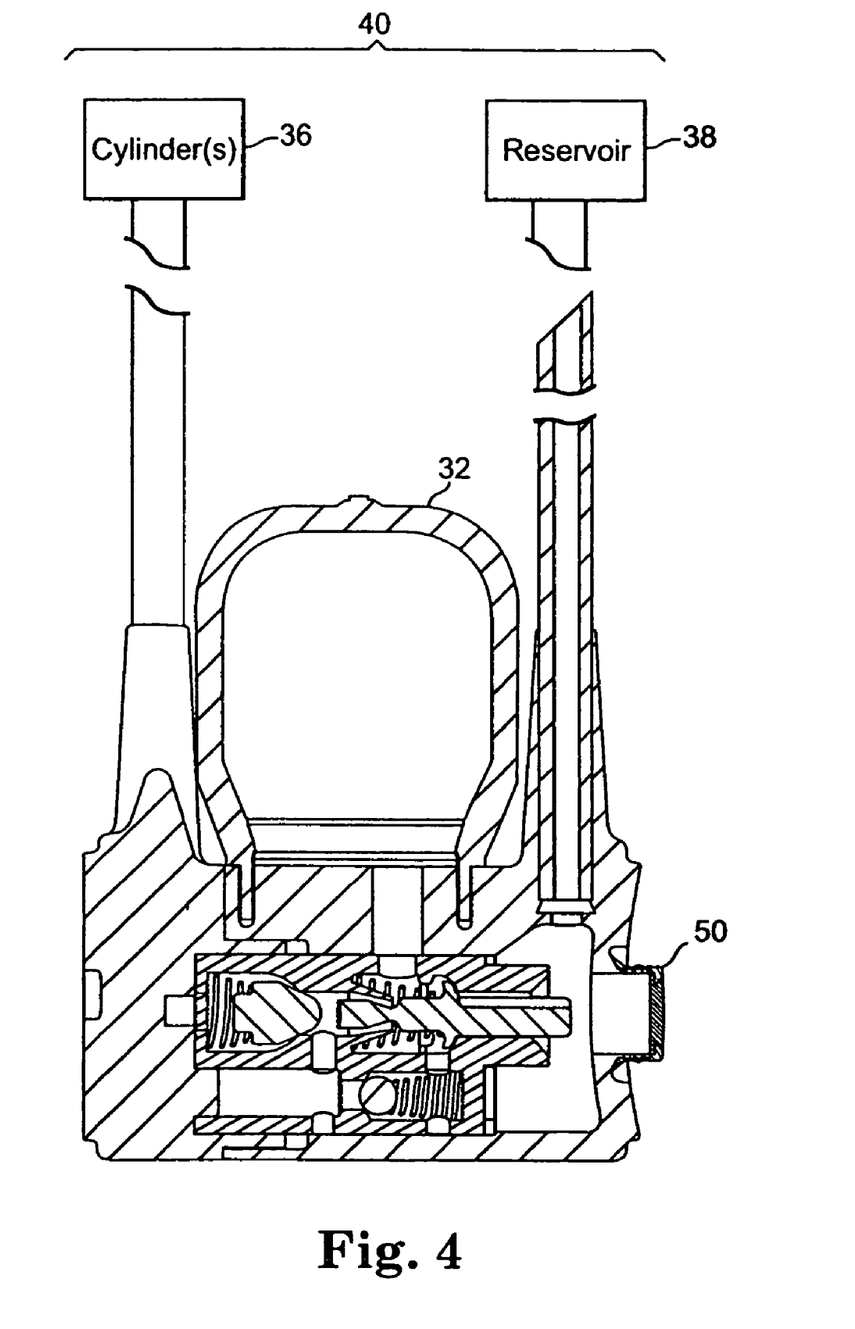
FIG. 4 is a schematic view of another three piece embodiment of the present invention showing a fluid septum in a location different than that of the embodiment shown in FIG. 1.
Figure 5:
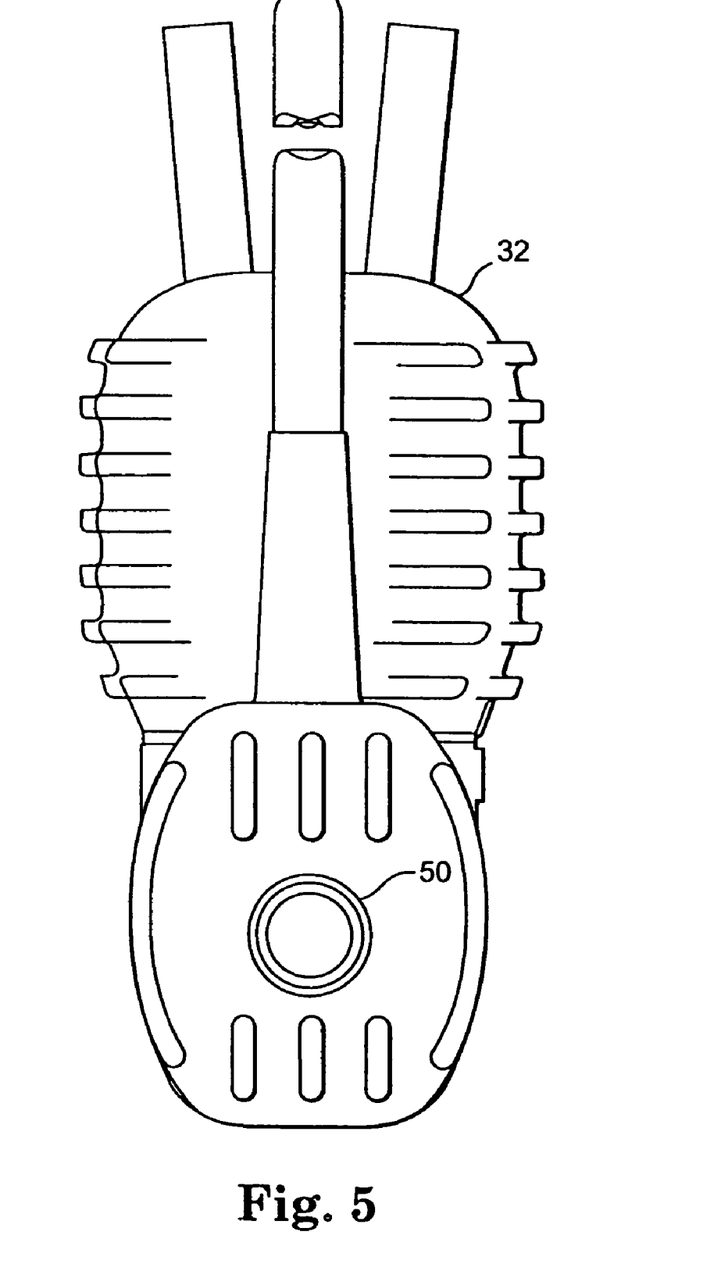
FIG. 5 is an end view of the embodiment of FIG. 4.

The present invention contemplates that the septum may be placed in a variety of different locations. Referring to FIGS. 4 and 5, there is shown another embodiment of system 40 according to the present invention. The system 40 includes cylinder(s) 36, reservoir 38, pump with pump bulb 32 and a septum 50. The septum 50 is located on the side of the pump assembly instead of in the walls of the pump bulb (as shown in FIG. 1). Alternatively, the septum may be located on a cylinder. While one septum is preferred, a plurality of septums, at different locations, may also be employed in accordance with the present invention.

Figure 6:
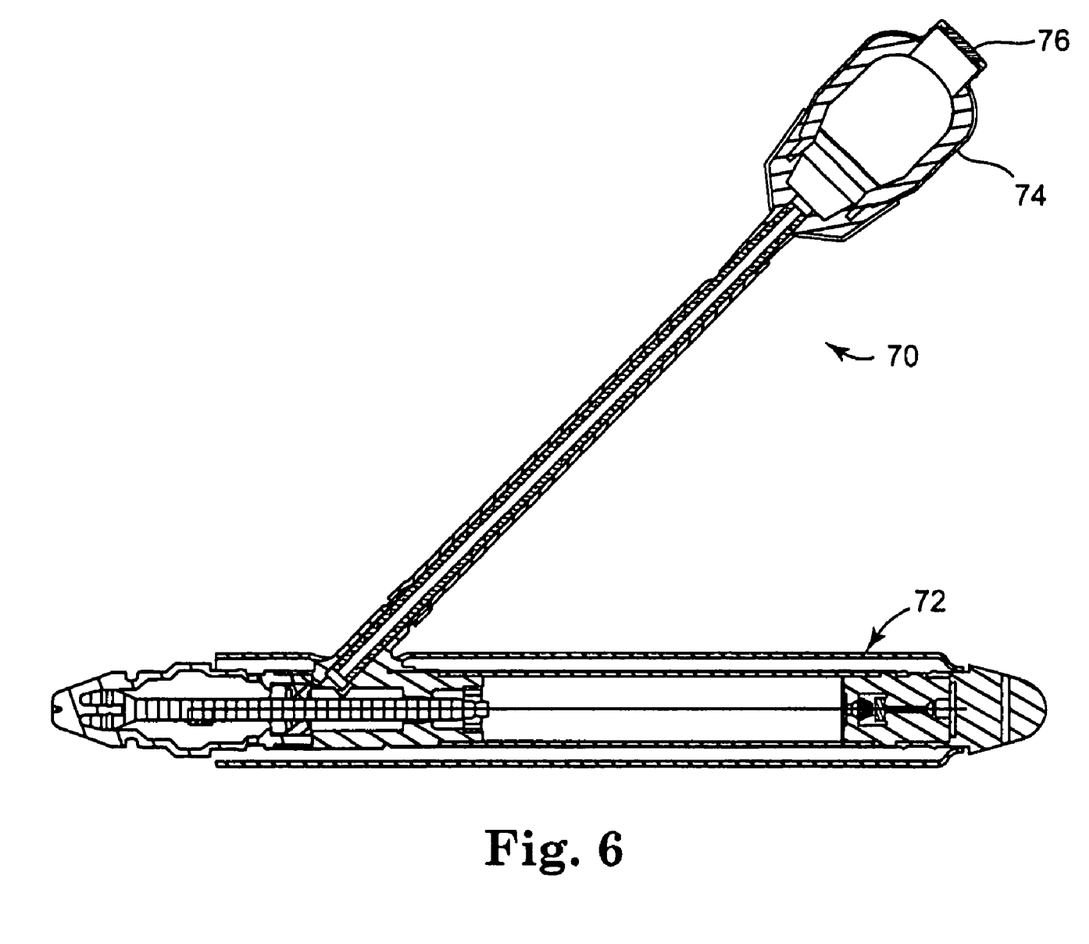
FIG. 6 is a side view of a two piece embodiment of the present invention.

The present invention may be utilized in both two piece and three piece penile prosthesis systems. FIG. 6 illustrates a two piece system comprising inflatable cylinder(s), an inflatable pump bulb 74 and a septum 76. Having a septum 76 on a two piece system affords fully distended capsule formation on the proximal corporal reservoir.

In another embodiment, the septum 20 affords a method of injecting an antibiotic or antimicrobial solution into the device for the treatment of device infection with standard antibiotics or other proprietary treatment methods. The invention comprises a system for restoring erectile function comprising a pump, cylinder(s), tubing and a reservoir, a fluid circuit within the system containing fluid, a septum, and an antimicrobial or antibiotic within the fluid placed by inserting a needle through the septum and injecting the antimicrobial or antibiotic. For example, the antimicrobial or antibiotic may comprise rifampin and minocycline. Suitable antimicrobials or antibiotics are disclosed in U.S. Pat. Nos. 5,624,704; 5,756,145; 5,902,283, 6,162,487 and 6,534,112.

Alternatively, an antimicrobial may comprise an iodine containing compound. This would avoid opening and remaking a connection or, as is often necessary, addition a piece of tubing and adding new connectors.

Figure 7:
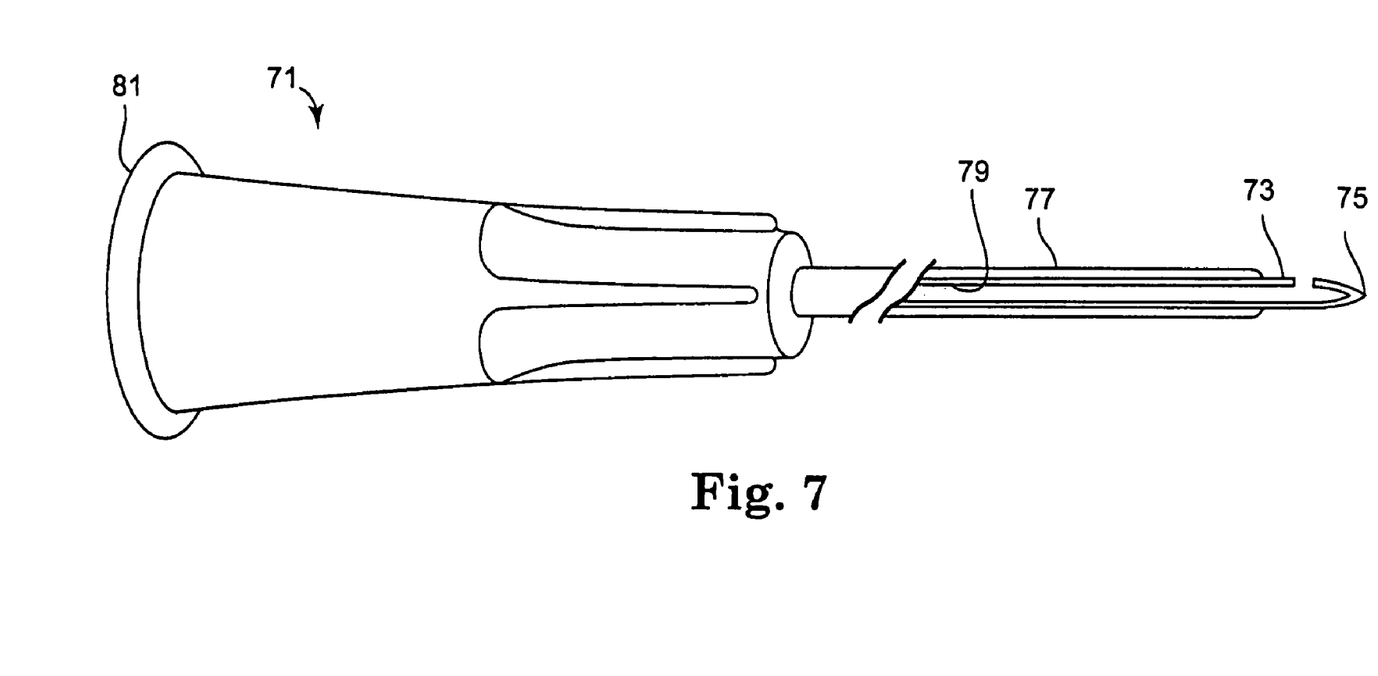
FIG. 7 is a schematic view of a component of a probe assembly according to an aspect of the present invention.
Figure 8:
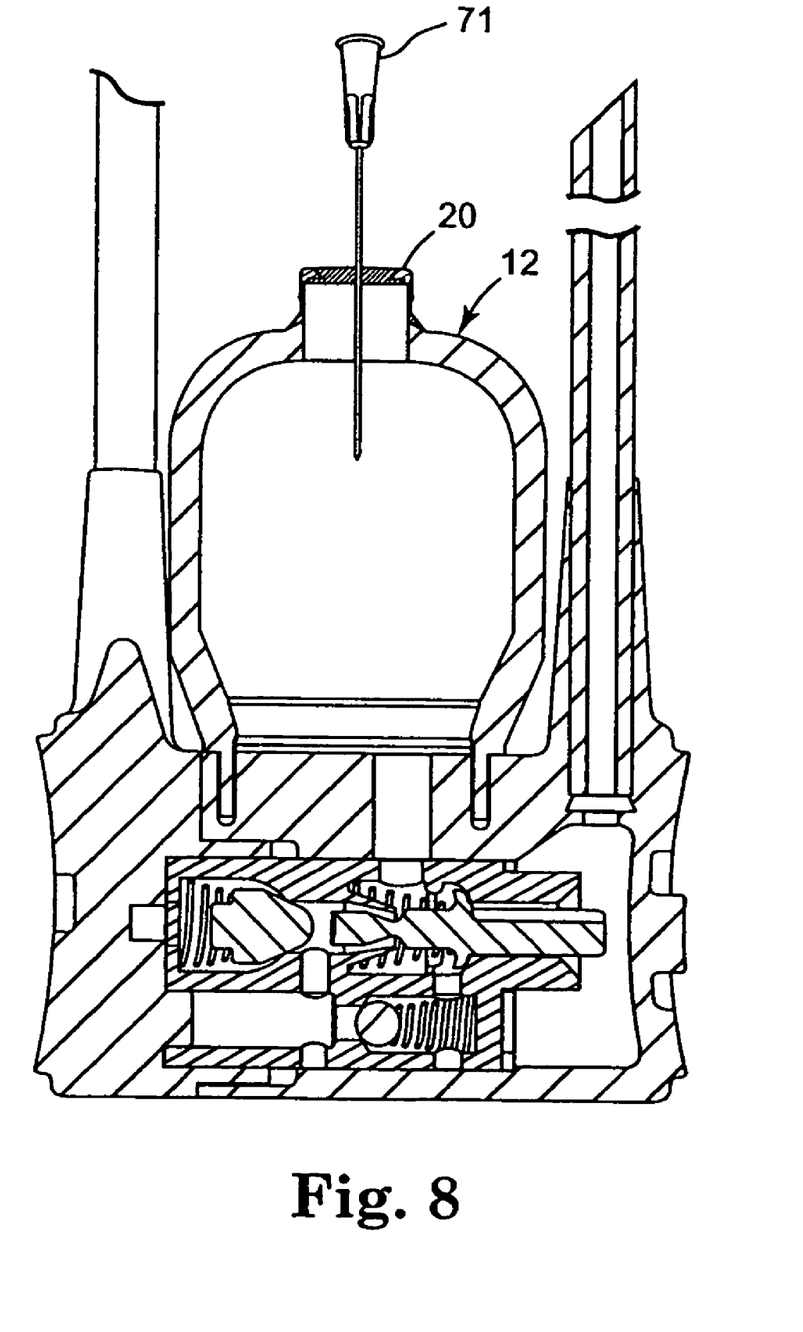
FIG. 8 is a schematic view of the probe of FIG. 7 being inserted into the septum of FIG. 1.

Referring now to FIGS. 7 and 8, the septum 20 affords post-operative confirmation of device complications (e.g. such as leakage or infection). In another aspect, the invention comprises a method of detecting an unsatisfactory condition of an inflatable penile prosthesis system (e.g. 10) comprising a pump 12, cylinder(s), fluid circuit, septum 20 and a reservoir.

FIG. 7 shows a sensor 71 including a non-coring needle or needle-like structure 73 (e.g. of conductive material) for traversing the septum, a non-coring tip 75, a non-conducting shaft 77 and a lumen 79 for adding or withdrawing fluid. The shaft 77 has an insulating or non conductive coating or surface on all or most of the exterior of the needle-like structure 73. The sensor 71 may optionally include a luer lock hub 81 for attachment to a syringe for adding or removing fluid including antibiotic or antimicrobial.

Another method of the invention comprises the steps of: implanting the inflatable penile prosthesis system 10 in a patient; providing a probe assembly with first and second sensors; placing the first sensor through the septum and into the fluid circuit of the inflatable penile prosthesis system; placing a second sensor outside the penile prosthesis system in the patient's tissue, sensing conditions with the first and second sensors, and comparing the conditions sensed by the first and second sensors to detect an unsatisfactory condition. The unsatisfactory condition may comprise fluid leakage or infection. The first and second sensors may be capable of sensing pH, electrical resistance or electrical potential.

Figure 9:
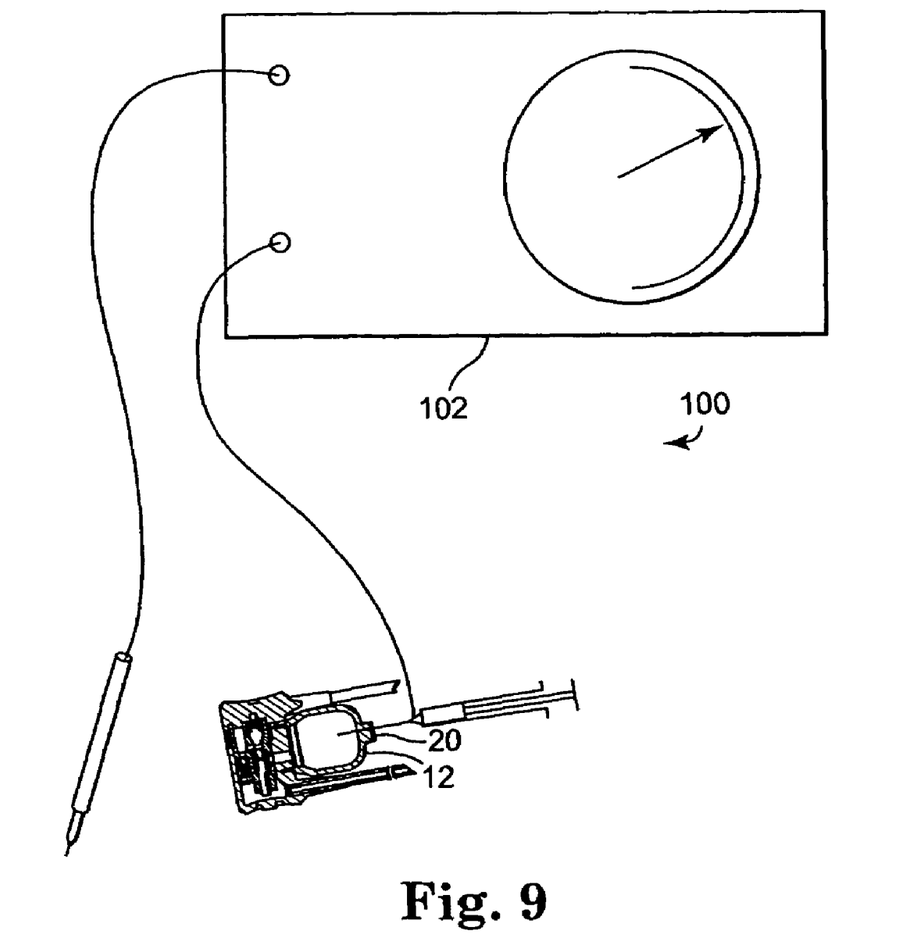
FIG. 9 is a schematic view showing a probe assembly and portions of a penile prosthesis assembly according to an aspect of the present invention.

Referring to FIG. 9, in one embodiment, a probe system 100 may comprise an ohmmeter 102. First and second sensors are shown in FIG. 9.

In another embodiment, at least one of the first and second sensors is integrated into the inflatable penile prosthesis system, and the probe system includes means for communicating with the sensor integrated into the inflatable penile prosthesis system. For example, the means for communicating with the sensor may include a probe for establishing electrical contact with the sensor. Alternatively, the means may comprise remote sensors such as pressure switches, or magnetostrictive ferromagnetic materials. For example, magnetostrictive and ferromagnetic materials an remote interrogation mechanisms are disclosed in U.S. Pat. No. 5,745,039.

A septum may also be used to test for unsatisfactory conditions associated with a device (e.g. leakage) through electrical conductivity testing or refilling the device with radio-opaque solutions where the device was originally filled with saline. The electrical conductivity testing could be accomplished through the use of a polymer-coated needle such as the needle 71. The polymer coating 77 provides insulation to the tissues being punctured, while the shaft 73 of the needle provides the electrical path to the center of the device. Needle designs or electrode patches that create the remaining part of the circuit may be used. To test for an infection (e.g. inside the prosthesis), a surgeon could pass a needle 71 through the skin and through the septum 20 and withdraw fluid for culturing. Later, with another needle pierce, the surgeon could inject the appropriate amount of antibiotic. Alternatively, the antibiotic may be injected prophylactically prior to culturing. The fluid pressure within the system may optionally be monitored.

FIG. 8 illustrates the needle 71 puncturing septum 20. This places the needle-like sensor 71 into the prosthesis with the tip fo the probe communicating with the interior of the prosthesis.

In another aspect, the present invention comprises the step of using a penile prosthesis to generate elongation in penile corporal length of original implant or on revision implants. The ability to have a penile prosthesis that can expand in girth and length has been demonstrated in product literature. However, the present invention comprises the novel steps of placing a septum on a penile device and combining it with cylinders that expand in length and girth. The method can create a lengthening in penile shaft length through tissue modeling or tissue engineering. This may have application for plastic surgery for the creation or restoration of a phallus in cases of severe trauma, penile cancer or ambiguous genitalia.

The present invention also comprises a method of treating corporal shortening normally seen following removals of the implant. In another aspect, the present invention comprises treating patients who have had device removals (e.g. due to infections) where a new device is not or cannot immediately be implanted, or by patient or physician preference is not implanted. An unsatisfactory condition to implant at the time of revision surgery may result in subsequent scarring and shortening of penile shaft length. Upon revision surgery, the physician can normally place a cylinder of smaller diameter than originally implanted often the rear tip of the prosthesis requires a so called "narrow base" implant. What is disclosed is the capability of now using a "narrow base prosthesis" with elongation capability to regain lost corporal length.

Several surgical methods are contemplated herein. A variety of different surgical approaches are contemplated herein including infrapubic and penoscrotal approaches. Such procedures are disclosed, for example, in the Operating Room Manual for the AMS 700™ Penile Prosthesis, available from American Medical Systems of Minnetonka, Minn., © 2001.

All patents, patent applications, and publications cited herein are hereby incorporated by reference in their entirety as if individually incorporated.

The present invention has now been described with reference to several embodiments. The foregoing detailed description and examples have been given for clarity of understanding only. Those skilled in the art will recognize that many changes can be made in the described embodiments without departing from the scope and spirit of the invention. Thus, the scope of the present invention should not be limited to the exact details and structures described herein, but rather by the appended claims and equivalents.

The invention claimed is:

1. A method of detecting an unsatisfactory condition of an inflatable penile prosthesis system comprising a pump, a cylinder, fluid circuit, a septum and a reservoir, the method comprising the steps of:

implanting the inflatable penile prosthesis system in a patient;

providing a probe assembly with first and second sensors;

placing the first sensor through the septum and into the fluid circuit of the inflatable penile prosthesis system;

placing a second sensor outside the penile prosthesis system in the patient's tissue, sensing conditions with the first and second sensors, and comparing the conditions sensed by the first and second sensors to detect an unsatisfactory condition.

2. A method according to claim 1 wherein the unsatisfactory condition is fluid leakage.

3. A method according to claim 1 wherein the unsatisfactory condition is infection.

4. A method according to claim 1 wherein the first and second sensors are capable of sensing pH.

5. A method according to claim 1 wherein the first and second sensors are capable of sensing electrical potential and the probe system comprises an ohmmeter.

6. A method according to claim 1 wherein the first and second sensors are capable of sensing resistance.

7. A method according to claim 1 wherein at least one of the first and second sensors is integrated into the inflatable penile prosthesis system, and the probe system includes means for communicating with the sensor integrated into the inflatable penile prosthesis system.

* * * * *